(12) United States Patent
Foster et al.

(10) Patent No.: US 6,588,254 B1
(45) Date of Patent: Jul. 8, 2003

(54) ROTARY RHEOMETER

(75) Inventors: Peter Foster, Redhill (GB); Nigel Doe, Dorking (GB)

(73) Assignee: Waters Investment Limited, New Castle, DE (US)

(*) Notice: Subject to any disclaimer, the term of this patent is extended or adjusted under 35 U.S.C. 154(b) by 0 days.

(21) Appl. No.: 10/108,351

(22) Filed: Mar. 29, 2002

(51) Int. Cl.[7] .................................................. G01N 11/10
(52) U.S. Cl. ...................................... 73/54.23; 73/54.38
(58) Field of Search ............................. 73/54.23, 54.28, 73/54.29, 54.3, 54.31, 54.32, 54.33, 54.34, 54.38, 54.37, 54.39

(56) References Cited

U.S. PATENT DOCUMENTS

| | | | |
|---|---|---|---|
| 1,658,950 A | 2/1928 | Stein | |
| 2,096,222 A | * 10/1937 | Bock | 73/54.35 |
| 2,382,979 A | 8/1945 | Demb | |
| 2,437,194 A | 3/1948 | Harrington | |
| 2,703,006 A | * 3/1955 | Savins | 73/54.33 |
| 2,807,160 A | 9/1957 | Asbeck | |
| 2,982,132 A | 5/1961 | Mendlowitz | |
| 3,435,666 A | 4/1969 | Fann | |
| 3,592,060 A | 7/1971 | Laverman | |
| 3,875,788 A | 4/1975 | Mills | |
| 3,935,726 A | 2/1976 | Heinz | |
| 3,962,907 A | 6/1976 | Peyrouset et al. | |
| 4,185,493 A | 1/1980 | Frosch et al. | |
| 4,379,775 A | 4/1983 | Brandstetr et al. | |
| 4,445,365 A | 5/1984 | Selby | |
| 4,466,276 A | 8/1984 | Ruyak et al. | |
| 4,468,953 A | * 9/1984 | Garritano | 73/54.39 |
| 4,612,799 A | 9/1986 | Choi et al. | |
| 4,630,468 A | 12/1986 | Sweet | |
| 4,633,708 A | 1/1987 | Bloommaert | |
| 4,643,021 A | 2/1987 | Mattout | |
| 4,878,377 A | 11/1989 | Abel | |
| 5,167,143 A | 12/1992 | Brookfield | |
| 5,223,227 A | 6/1993 | Zuckerman | |
| 5,308,953 A | 5/1994 | Grudzein, Jr. et al. | |
| 5,526,681 A | 6/1996 | Selby | |
| 5,587,522 A | 12/1996 | Selby | |
| 5,777,212 A | 7/1998 | Sekiguchi et al. | |
| 6,164,818 A | * 12/2000 | Dick et al. | 73/54.39 |
| 6,240,770 B1 | 6/2001 | Raffer | |

FOREIGN PATENT DOCUMENTS

| | | |
|---|---|---|
| FR | 2 389 884 | 1/1979 |
| SU | 1392-453 | 4/1986 |
| SU | 1769-083 | 10/1992 |
| WO | WO94/20832 | 9/1994 |

OTHER PUBLICATIONS

Physica MCR 300, Modular Compact Rheometer Manual. Apr. 1999.
TA Instruments Rheometers Manual, No Date.

* cited by examiner

*Primary Examiner*—Edward Lefkowitz
*Assistant Examiner*—Michael Cygan
(74) *Attorney, Agent, or Firm*—Shaw Pittman LLP

(57) ABSTRACT

A rotary rheometer having a concentric cylinder control jacket and a sample cup. The sample cup fits snugly inside the control jacket, such that the sample cup is in substantial thermal contact with the control jacket along at least the greater part of the length of the sample cup. A heating/cooling assembly such as a Peltier plate, positioned, for example, beneath the control jacket, is used to heat and/or cool the control jacket, thus heating and cooling the sample cup. The sample cup includes a generally annular chamber, which ensures that the sample experiences a uniform temperature. The rheometer reaches steady-state sample temperature more quickly, and the steady-state temperature reached is closer to the actual desired sample temperature than with prior art rheometers, due to the much greater thermal contact between the sample cup and the control jacket.

29 Claims, 9 Drawing Sheets

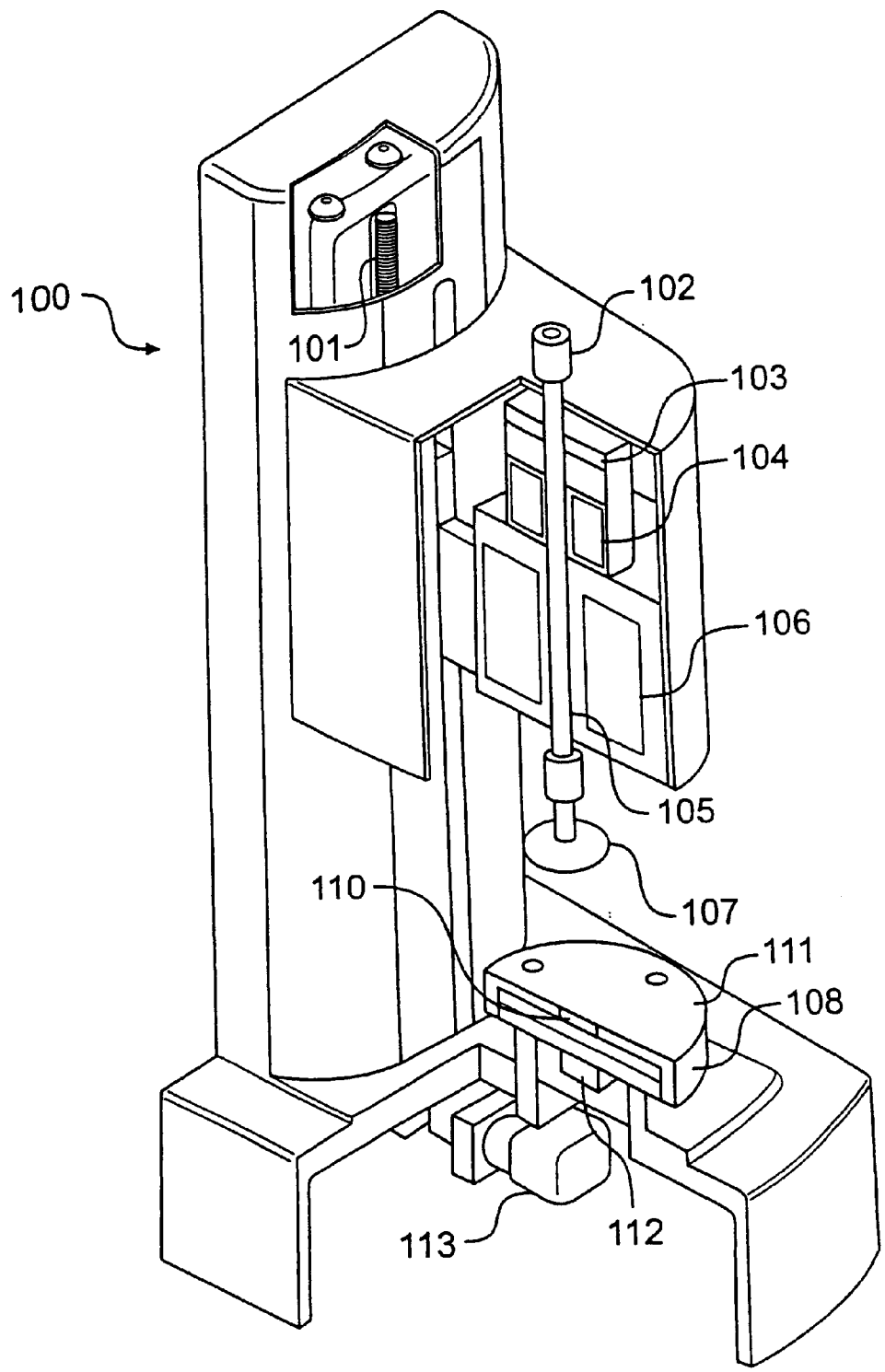
PRIOR ART
*FIG. 1A*

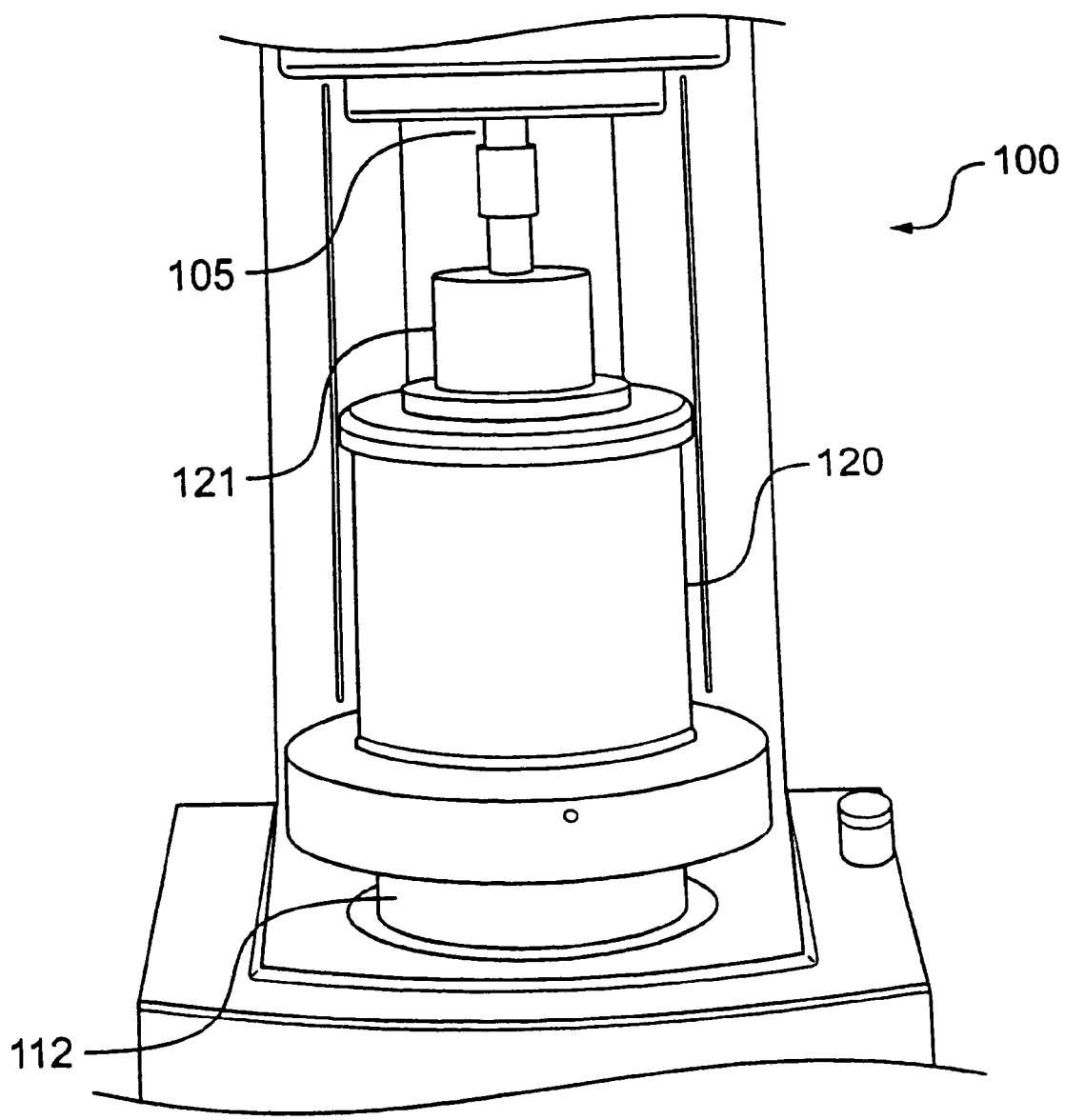
PRIOR ART
*FIG. 1B*

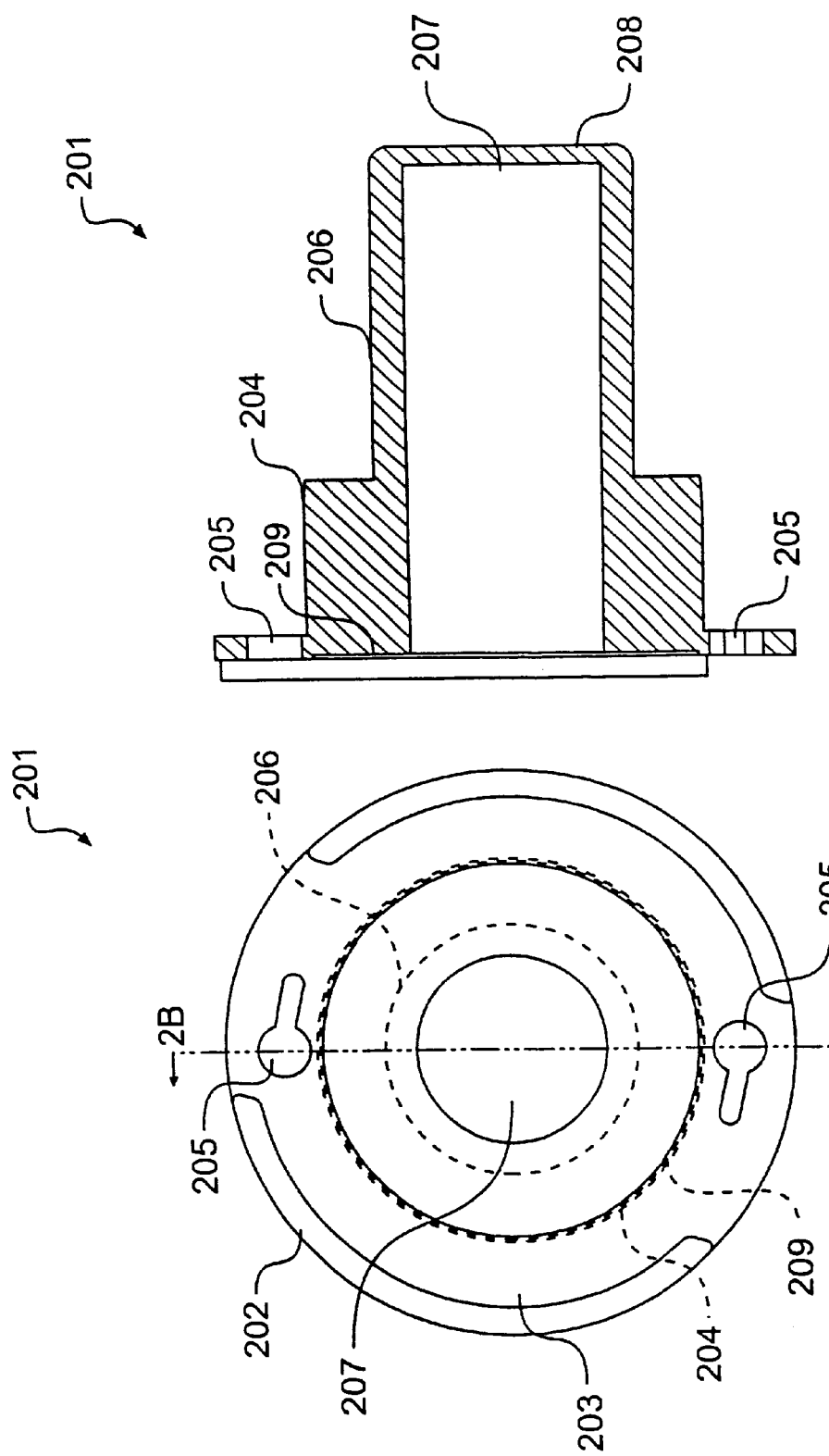
FIG. 2A PRIOR ART
FIG. 2B PRIOR ART

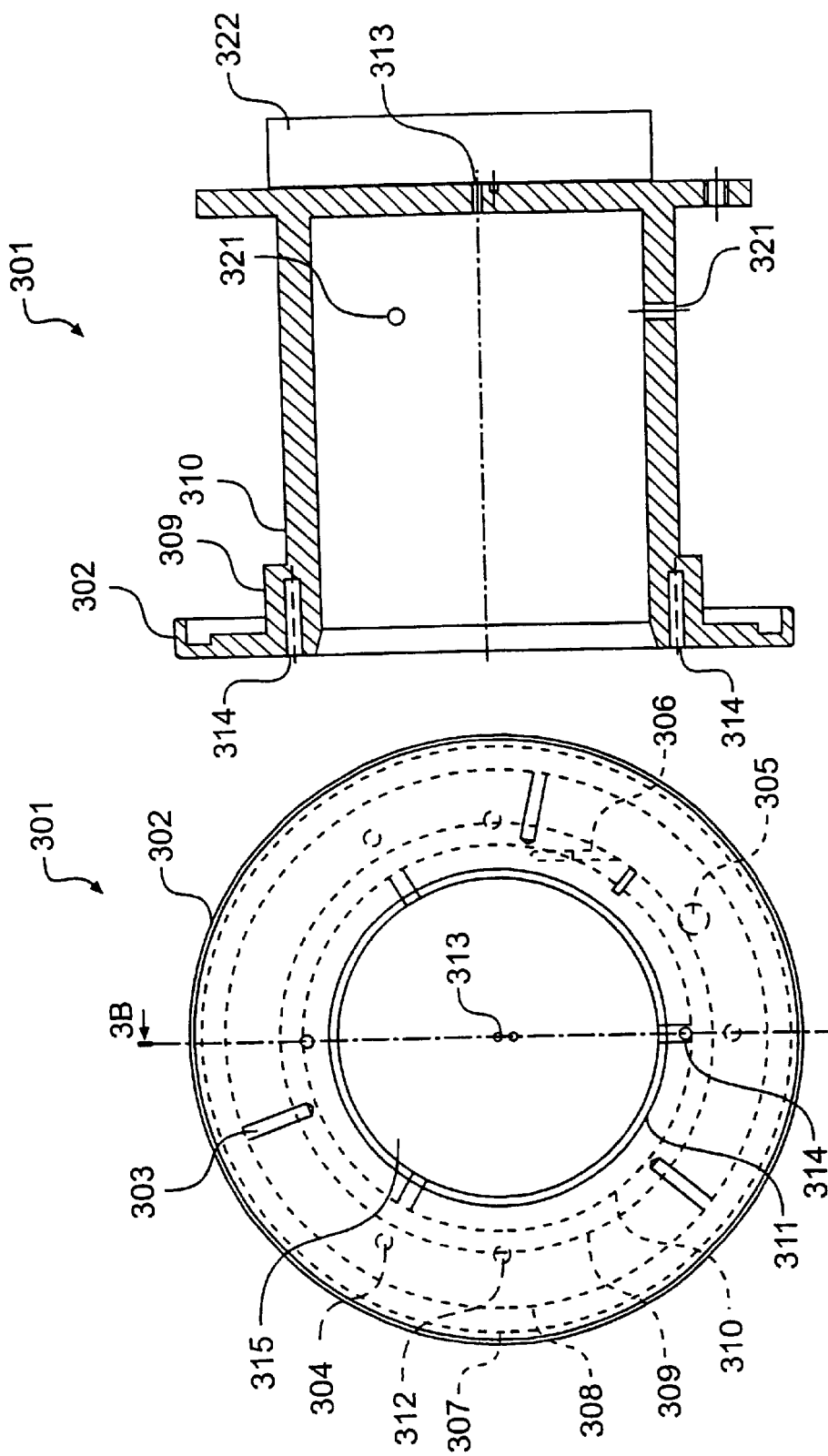
PRIOR ART
FIG. 3A
PRIOR ART
FIG. 3B

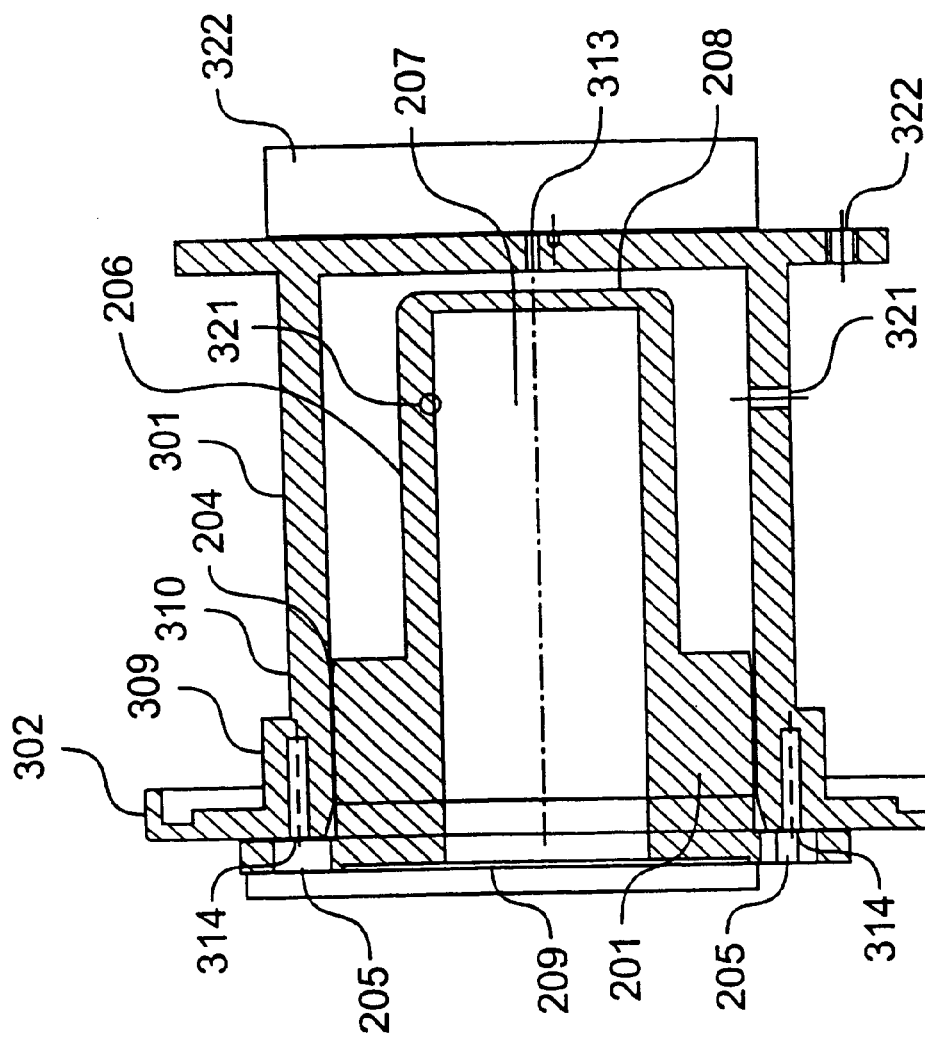
FIG. 3C PRIOR ART

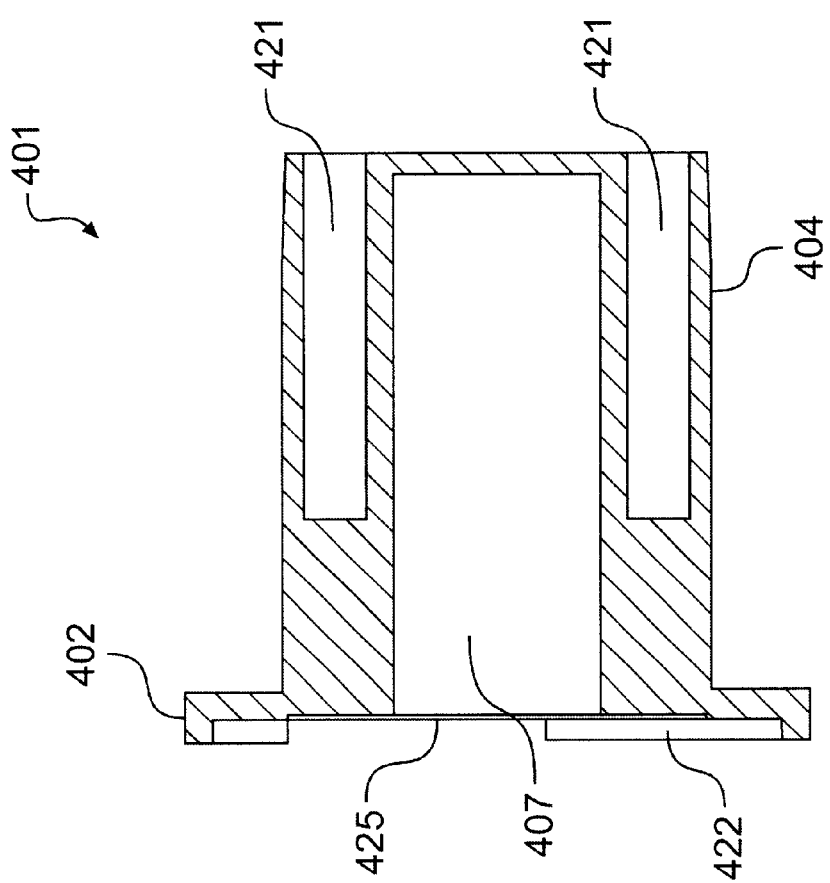
*FIG. 4B*
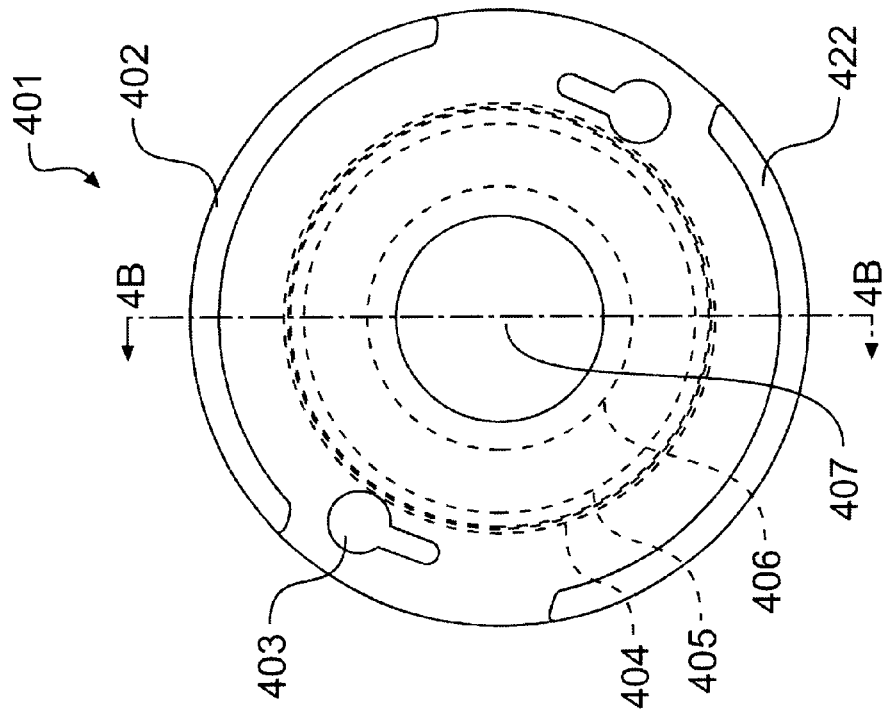
*FIG. 4A*

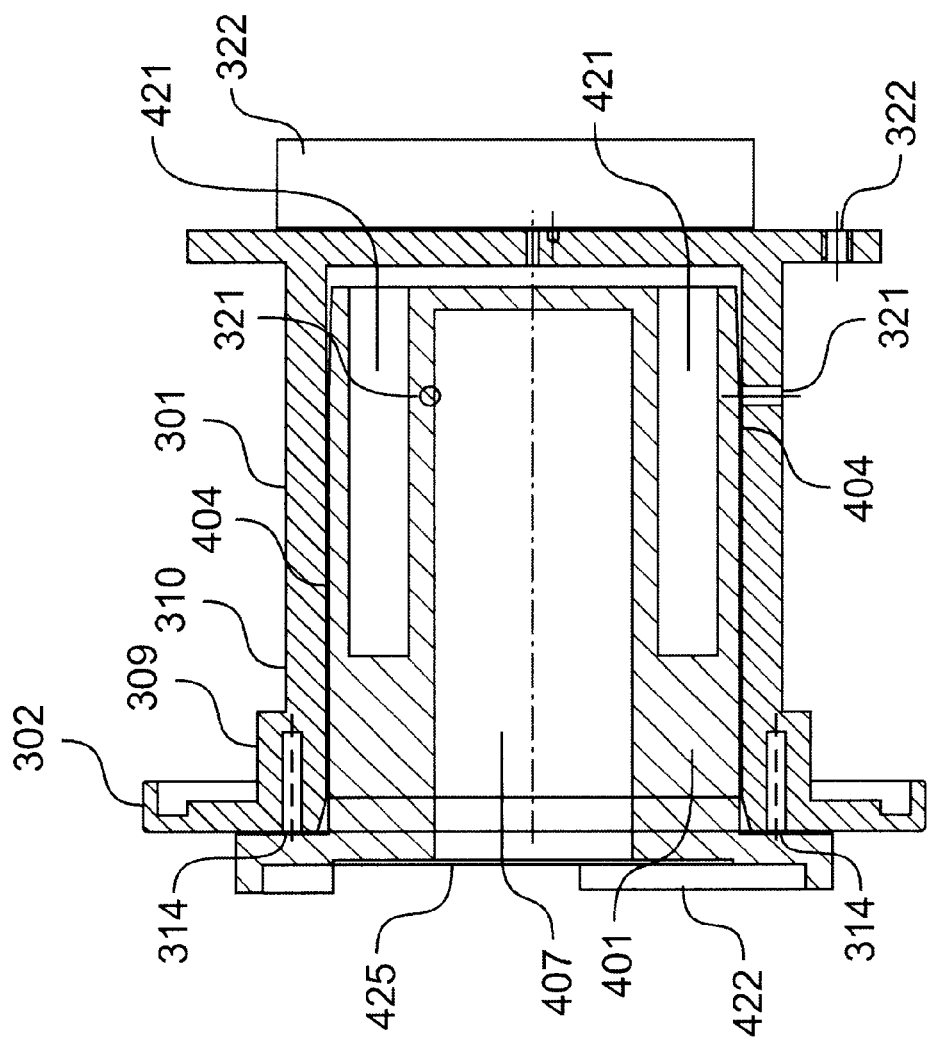
FIG. 4C

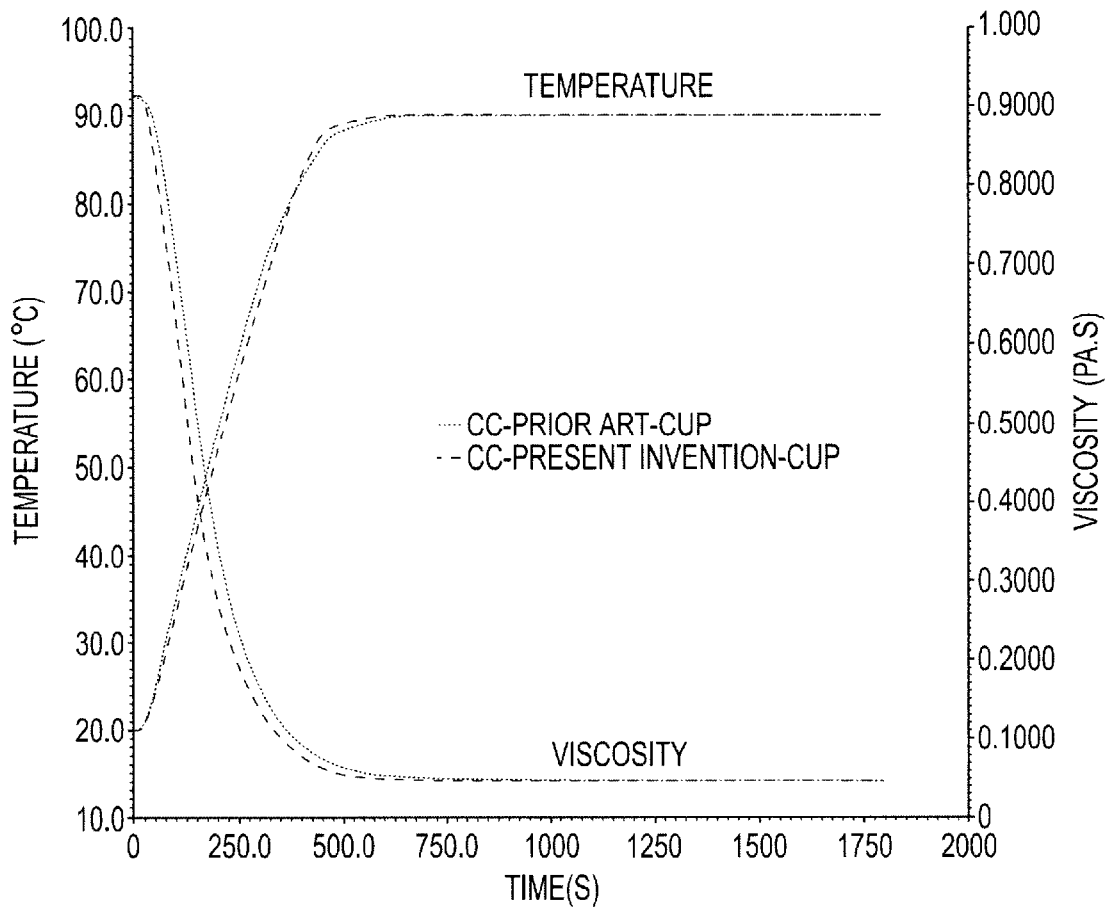
*FIG. 5A*

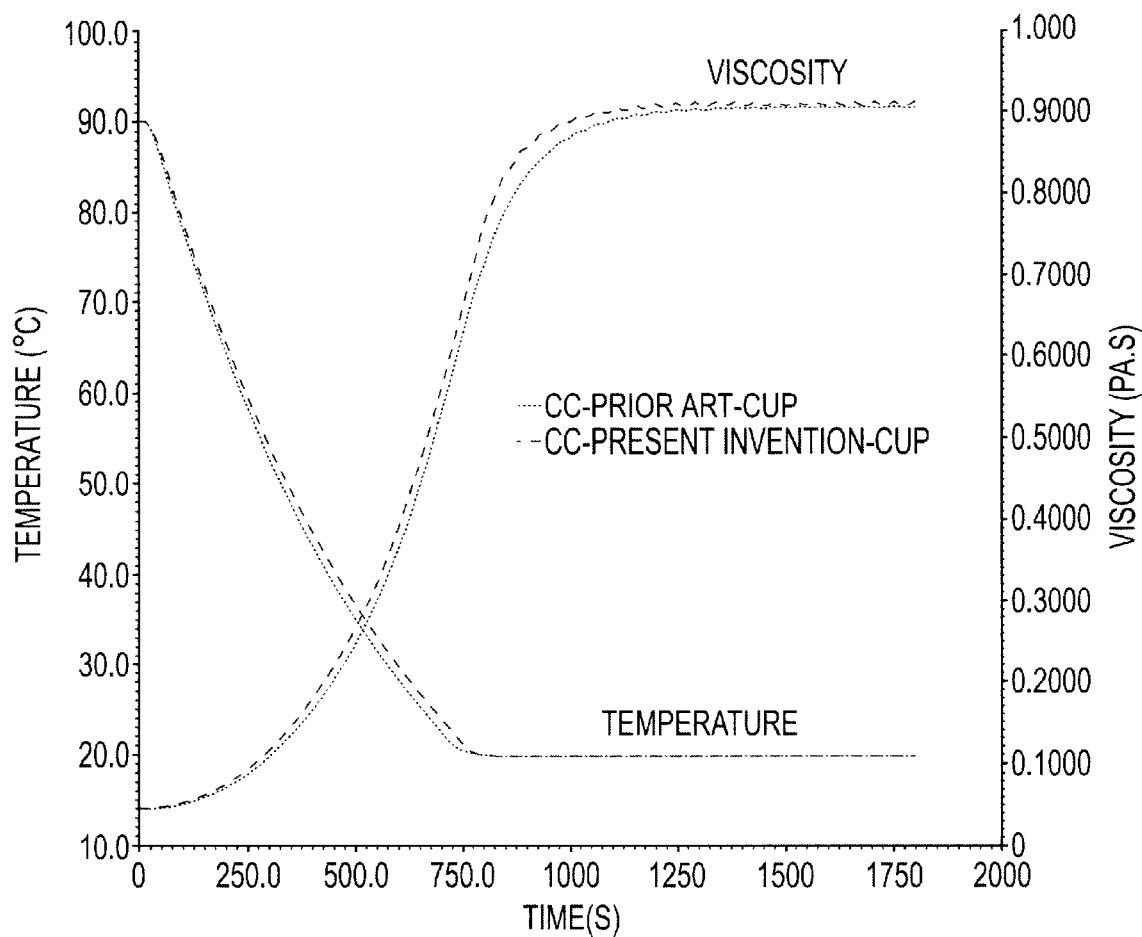
FIG. 5B

ROTARY RHEOMETER

BACKGROUND

1. Field of the Invention

The present invention relates generally to rheometers, which are used to characterize materials by measuring the materials viscosity, elasticity, shear thinning, yield stress, compliance and/or other material properties.

2. Background of the Invention

Rotary rheometers, viscometers or viscosimeters are used to measure fluid or other properties of materials such as their viscosity by rotating, deflecting or oscillating a measuring object in a material, and measuring, for example, the torque required to rotate or deflect or oscillate the object within the material. As used herein, the term "rheometer" shall mean rheometers, viscometers, viscosimeters and similar instruments that are used to measure the properties of fluid or similar (see list below) materials. The term "measuring object" shall mean an object having any one of several geometries, including, for example, cones, discs, vanes, parallel plates, concentric cylinders and double concentric cylinders. The materials may be liquids, oils, dispersions, suspensions, emulsions, adhesives, biological fluids such as blood, polymers, gels, pastes, slurries, melts, resins, powders or mixtures thereof. Such materials shall all be referred to generically as "fluids" herein. More specific examples of materials include asphalt, chocolate, drilling mud, lubricants, oils, greases, photoresists, liquid cements, elastomers, thermoplastics, thermosets and coatings. As is known to one of ordinary skill in the art, many different geometries may be used for the measuring object in addition to the cylinders, cones, vanes and plates listed above. The measuring objects may be made of, for example, stainless steel, anodized aluminum or titanium. U.S. Pat. Nos. 5,777,212 to Sekiguchi et al., 4,878,377 to Abel and 4,630,468 to Sweet describe various configurations, constructions and applications of rheometers.

The fluid properties of materials are generally dependent on their temperature. For that reason, it is generally important that the temperature of the material being tested is known and is homogeneous. If the temperature of the material being tested were not homogeneous, the accuracy and validity of the measurement would be seriously compromised. Thus the temperature of the fluid is generally accurately controlled, and is preferably made as homogeneous as possible, for example by using a fluid bath or a Peltier plate. Compared to a fluid bath, a Peltier plate temperature control system provides a more rapid heating and cooling of the sample, and is more economical, because it does not require an expensive controlled-temperature fluid circulator.

FIG. 1A is a schematic perspective view of a rotary rheometer 100, showing lead screw 101, draw rod 102, optical encoder 103, air bearing 104, drive shaft 105, drag cup motor 106, measuring object 107 (shown in FIG. 1A as a parallel plate), heating/cooling assembly (eg., a Peltier plate) 108, temperature sensor 110 (eg., a Pt temperature sensor), surface 111, normal force transducer 112, and auto gap set motor and encoder 113. FIG. 1B is a schematic drawing of a concentric cylinder configuration in position on the rheometer of FIG. 1A, showing the control jacket 120 of the concentric cylinder configuration on top of normal force transducer 112 of rheometer 100. FIG. 1B shows a cylindrical measuring object 121 (used in this configuration instead of the parallel plate measuring object 107 shown in FIG. 1A).

In operation, control jacket 120 contains sample cup 201. FIGS. 2A and 2B are schematic drawings of a top view and a cross-sectional view of a prior art sample cup. FIG. 2A shows sample cup 201, which has top flange 203 with top flange lip 202, and fixing holes 205. Sample cup 201 also includes sample bore 207 and cover location lip 209. Cover location lip 209 is used to locate a cover that may be used, if necessary, to minimize evaporation from the sample. FIG. 2A also shows the upper end 204 of the sample cup 201 and lower end 206 of sample cup 201. FIG. 2B shows the upper end 204 and the lower end 206 of sample cup 201, as well as fixing holes 205, sample bore 207, sample cup base 208 and location lip 209. The fixing holes are used to prevent rotation of the sample cup during a test run. As shown in FIGS. 2A and 2B, the upper end 204 of the sample cup has a larger outer diameter than its lower end 206.

FIGS. 3A and 3B are a top view and a cross-sectional view of a prior art control jacket 301. Control jacket 301 has fixing holes 303, 304, 312, and 314, top lip 302, cabling hole 305 and sensor hole 306. Fixing holes 314 are used in conjunction with holes 205 (shown in FIGS. 2A and 2B) to prevent rotation of the measuring cup. Fixing holes 312 are used to fix the heating/cooling assembly, fixing holes 304 are used to fix the lower mounting plate and fixing holes 303 are used to fix the outer sleeve/cover. Sensor holes 306 and 313 are used for temperature sensors. FIGS. 3A and 3B also show cover locations 307 and 308, sample cup location chamfer 311, the outer surfaces 309 and 3 10 of the control jacket and the main bore of the control jacket 315 (which is where sample cup 201 fits into control jacket 301) and air hole 321. Cover locations 307 and 308 are used to locate the cover/sleeve that fits over the outer jacket. FIG. 3B also shows the heating/cooling assembly 322, which is used to heat or cool the control jacket and the sample cup. For example, heating/cooling assembly 322 may be a Peltier plate.

As shown in FIG. 3C, in operation sample cup 201 fits inside control jacket 301, such that an isolation gap is formed between sample cup 201 and control jacket 301.

U.S. Pat. No. 6,240,770 to Raffer discloses a rotary viscosimeter having an isolation gap between a measuring cup and a temperature control cup. Because of the isolation gap, the measuring cup and the temperature control cup are in good heat conducting contact only in the vicinity of their upper circumferences, such that the heat conduction between the measuring cup and the temperature control cup is restricted to the upper ends of the measuring and control cups only. A heat pump, such as a Peltier block, is used to control the temperature of the temperature control cup so that heat is supplied to the measuring cup in a controlled manner via the mutual contact area at the upper ends of the measuring and control cups.

SUMMARY OF THE INVENTION

The present invention is a rotary rheometer having a concentric cylinder configuration. The concentric cylinder configuration includes a control jacket and a sample cup. The sample cup fits snugly inside the control jacket, such that the sample cup is in substantial thermal contact with the control jacket along at least twothirds of the length of the sample cup, and preferably along the greater part of the length of the sample cup (e.g., more than 80% of the length). The sample cup and the control jacket are fabricated from a good heat conducting material, such as, for example, HE30 aluminum. Copper or silver alloys or stainless steel could also be used. A heating/cooling assembly, positioned, for example, beneath the control jacket, is used to heat and/or cool the control jacket, thus heating and cooling the sample cup. In a preferred embodiment of the invention, the heating/cooling assembly is a Peltier plate. The sample cup includes a generally annular chamber, which ensures that the sample experiences a uniform temperature.

Preferably, the bottom of the sample cup is not in contact with the bottom of the control jacket, i.e., there is a gap between the bottom of the sample cup and the bottom of the control jacket such that there is a disk-shaped lower chamber that is in fluid communication with the annular chamber in the sample cup.

BRIEF DESCRIPTION OF THE DRAWINGS

FIG. 1A is a schematic diagram of a perspective view of a prior art rotary rheometer.

FIG. 1B is a schematic diagram of a concentric cylinder configuration in position on the rheometer of FIG. 1A.

FIG. 2A is a schematic diagram of a top view of a prior art sample cup.

FIG. 2B is a schematic diagram of a cross-sectional view of a prior art sample cup.

FIG. 3A is a schematic diagram of a top view of a control jacket.

FIG. 3B is a schematic diagram of a cross-sectional view of a control jacket.

FIG. 3C is a schematic diagram of a cross-sectional view of a sample cup in a control jacket.

FIG. 4A is a schematic diagram of a top view of a sample cup of the present invention.

FIG. 4B is a schematic diagram of a cross-sectional view of a sample cup of the present invention.

FIG. 4C is a schematic diagram of a cross-sectional view of the sample cup of the present invention in a control jacket.

FIGS. 5A and 5B are test data showing the improved performance of the rheometer of the present invention, compared to a rheometer using the sample cup of FIGS. 2A and 2B.

DETAILED DESCRIPTION OF THE INVENTION

FIGS. 4A, 4B and 4C are schematic diagrams that show the sample cup of the present invention as it fits into the control jacket. FIGS. 4A and 4B show sample cup 401, with fixing holes 403, top flange lips 402 and 422, outer surface 404 of the sample cup, annular chamber 421 (which has outer diameter 405 and inner diameter 406), cover location 425 and sample bore 407.

FIG. 4C shows sample cup 401 as it fits into control jacket 301, such that there is good thermal contact between sample cup 401 and control jacket 301 along at least two-thirds of the length of the sample cup, and preferably along the greater part of the length of sample cup 401 (e.g., more than 80% of the length). As best seen in FIG. 4C, the lower end of sample cup 401 (to the right in FIG. 4C) has a very slight taper, so as to facilitate insertion of sample cup 401 into jacket 301. The length of the taper should be limited, preferably to no more than, for example, about 15 mm.

Typically, there is an air gap of at least 3 mm, preferably 5–10 mm and more preferably about 7 mm, depending on the sample cup used, between the bottom of the sample cup and the bottom of the control jacket. Annular chamber 421 is at least 3 mm wide, and preferably about 8–10 mm wide. The maximum width possible for annular chamber 421 is dictated by mechanical considerations—the inner and outer walls of sample cup 401 must be thick enough so that they can be machined and still maintain their cylindrical shapes, and so that there is good thermal conduction along the inner and outer walls of sample cup 401. As an example, sample cup 401 can have an inner diameter (ID) of about 30 mm and an outer diameter (OD) of about 62.5 mm. The OD of sample cup 401 must, of course, be selected such that sample cup 401 slides into control jacket 301 such that there is good thermal contact between sample cup 401 and control jacket 301 when the sample cup is in position in the control jacket. Annular chamber 421 can have an ID of about 38 mm and an OD of about 56 mm. In that case, annular chamber 421 would be about 9 mm wide, the inner wall of sample cup 421 would be about 4 mm thick and the outer wall would be about 3.25 mm thick. The height of the annular chamber is preferably at least twothirds of the height of the sample cup.

Performance

The rheometer of the present invention has two important advantages over the prior art rheometer using the sample cup shown in FIGS. 2A and 2B: the sample temperature reaches the steady-state temperature more quickly, and the steady-state temperature reached is closer to the actual desired sample temperature, as shown by the tests described below. These improvements in performance are due to the much greater thermal contact between the sample cup and the control jacket, compared to the prior art. Moreover, the present invention achieves these improvements in performance without introducing negative effects, such as an increase in the thermal mass of the apparatus or an increase in the temperature gradients in the sample cup.

The improved performance of the rheometer of the present invention, compared to prior art rheometers using the sample cup of FIGS. 2A and 2B is shown in FIGS. 5A and 5B. FIGS. 5A and 5B are plots of the temperature and viscosity of a sample as measured by a prior art rheometer (dotted lines) and as measured by a rheometer of the present invention (dashed lines). FIG. 5A is a plot of the temperature and viscosity of the sample as the temperature is increased from 20° C. to 90° C. FIG. 5B is a plot of the temperature and viscosity of the sample as the temperature is decreased from 90° C. to 20° C. As can be seen from both FIGS. 5A and 5B, the sample reaches its final temperature more quickly and the measured viscosity of the sample reaches its final value more quickly with the rheometer of the present invention than with the rheometer using the prior art sample cup of FIGS. 2A and 2B.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

What is claimed is:

1. A rheometer comprising:
   (a) a control jacket having an inner wall;
   (b) a sample cup comprising an annular chamber, wherein said sample cup has an outer wall; and
   (c) a heating/cooling assembly positioned below the control jacket in thermal contact with the control jacket, wherein the outer wall of the sample cup and the inner wall of the control jacket are in substantial thermal and physical contact along at least two-thirds of the length of the outer wall of the sample cup.

2. The rheometer of claim 1, further comprising a lower chamber in fluid communication with the annular chamber in the sample cup.

3. The rheometer of claim 2, wherein the height of the lower chamber is 3 to 10 mm.

4. The rheometer of claim 2, wherein the height of the lower chamber is about 7 mm.

5. The rheometer of claim 1, wherein the outer wall of the sample cup and the inner wall of the control jacket are in substantial thermal and physical contact along the greater part of the length of the outer wall of the sample cup.

6. The rheometer of claim 1, wherein the width of the annular chamber is at least 3 mm wide.

7. The rheometer of claim 1, wherein the width of the annular chamber is 8 to 10 mm.

8. The rheometer of claim 1, wherein the heating/cooling assembly is a Peltier plate assembly.

9. A rheometer assembly comprising:
   (a) a sample cup having an annular chamber within;
   (b) a control jacket having a central bore; and
   (c) a lower chamber in fluid communication with the annular chamber formed by the outer surface of the bottom of the sample cup and the inner surface of the bottom of the control jacket,
     wherein the outer diameter of the sample cup is dimensioned to fit into the central bore of the control jacket, such that there is good thermal and physical contact along at least two-thirds of the length of the sample cup, and
     wherein the height of the annular chamber is at least two-thirds of the height of the sample cup.

10. The rheometer assembly of claim 9, wherein there is good thermal and physical contact between the sample cup and the control jacket along the greater length of the sample cup.

11. The rheometer assembly of claim 9, wherein the width of the annular chamber is at least 3 mm.

12. The rheometer assembly of claim 9, wherein the width of the annular chamber is 8 to 10 mm.

13. The rheometer assembly of claim 9, wherein the height of the lower chamber is at least 3 mm.

14. The rheometer assembly of claim 9, wherein the height of the lower chamber is about 7 mm.

15. The rheometer assembly of claim 9, wherein the control jacket comprises a sensor hole in its bottom end.

16. The rheometer assembly of claim 9, wherein the control jacket comprises at least one air hole.

17. A rheometer comprising:
   (a) a control jacket having an inner wall;
   (b) a sample cup comprising an annular chamber, wherein said sample cup has an outer wall; and
   (c) a heating/cooling assembly positioned below the control jacket in thermal contact with the control jacket,
     wherein the outer wall of the sample cup and the inner wall of the control jacket are in substantial thermal contact along at least two-thirds of the length of the outer wall of the sample cup, and
     wherein the lower end of the sample cup is tapered.

18. The rheometer of claim 17, further comprising a lower chamber in fluid communication with the annular chamber in the sample cup.

19. The rheometer of claim 17, wherein the heating/cooling assembly is a Peltier plate assembly.

20. The rheometer of claim 17, wherein the outer wall of the sample cup and the inner wall of the control jacket are in substantial thermal contact along the greater part of the length of the outer wall of the sample cup.

21. A rheometer assembly comprising:
   (a) a sample cup having an annular chamber within;
   (b) a control jacket having a central bore; and
   (c) a lower chamber in fluid communication with the annular chamber formed by the outer surface of the bottom of the sample cup and the inner surface of the bottom of the control jacket,
     wherein the outer diameter of the sample cup is dimensioned to fit into the central bore of the control jacket, such that there is good thermal contact along at least two-thirds of the length of the sample cup,
     wherein the height of the annular chamber is at least two-thirds of the height of the sample cup, and
     wherein the control jacket comprises a sample cup location chamfer at the upper end of its central bore.

22. The rheometer assembly of claim 21, wherein the lower end of the sample cup has a taper for facilitating insertion of the sample cup into the control jacket.

23. The rheometer assembly of claim 21, wherein there is good thermal contact between the sample cup and the control jacket along the greater length of the sample cup.

24. The rheometer assembly of claim 21, wherein the control jacket comprises a sensor hole in its bottom end.

25. The rheometer assembly of claim 21, wherein the control jacket comprises at least one air hole.

26. A rheometer assembly comprising:
   (a) a sample cup having an annular chamber within;
   (b) a control jacket having a central bore; and (c) a lower chamber in fluid communication with the annular chamber formed by the outer surface of the bottom of the sample cup and the inner surface of the bottom of the control jacket,
     wherein the outer diameter of the sample cup is dimensioned to fit into the central bore of the control jacket, such that there is good thermal contact along at least two-thirds of the length of the sample cup,
     wherein the height of the annular chamber is at least two-thirds of the height of the sample cup, and
     wherein the lower end of the sample cup has a taper for facilitating insertion of the sample cup into the control jacket.

27. The rheometer assembly of claim 26, wherein there is good thermal contact between the sample cup and the control jacket along the greater length of the sample cup.

28. The rheometer assembly of claim 26, wherein the control jacket comprises a sensor hole in its bottom end.

29. The rheometer assembly of claim 26, wherein the control jacket comprises at least one air hole.

* * * * *